United States Patent [19]

Youssef

[11] Patent Number: 4,491,994

[45] Date of Patent: Jan. 8, 1985

[54] WILD BEE NESTING DOMICILE

[76] Inventor: Nabil N. Youssef, 2168 N. 1450 East, North Logan, Utah 84321

[21] Appl. No.: 520,472

[22] Filed: Aug. 4, 1983

[51] Int. Cl.³ ............................................. A01K 47/00
[52] U.S. Cl. ........................................ 6/1; 428/181
[58] Field of Search ...................... 6/1, 10, 11; 119/1; 428/181

[56] References Cited

U.S. PATENT DOCUMENTS

| | | | |
|---|---|---|---|
| 2,410,744 | 11/1946 | Powers | 428/178 |
| 2,575,898 | 11/1951 | Tadinger | 428/182 X |
| 3,212,956 | 10/1965 | Yoshikawa | 428/182 X |
| 3,486,485 | 12/1969 | Kahanick | 119/1 |
| 3,819,466 | 6/1974 | Winfield et al. | 428/182 X |
| 4,025,462 | 5/1977 | Cleveland | 428/182 X |
| 4,055,911 | 11/1977 | Aylor | 119/1 X |
| 4,207,637 | 6/1980 | Niebur | 6/1 |
| 4,257,134 | 3/1981 | Niebur | 6/1 |
| 4,289,513 | 9/1981 | Brownhill et al. | 428/182 X |
| 4,319,371 | 3/1982 | Wiederrich | 6/1 |

OTHER PUBLICATIONS

"Alfalfa Leafcutter Bees for Pollinating Alfalfa in Western Canada", G. A. Hobbs, Pub. No. 1495, Canadian Agricultural Dept., 1973.
"The Bords and the Bees", Advertising Flyer.

Primary Examiner—Robert P. Swiatek
Attorney, Agent, or Firm—A. Ray Osburn

[57] ABSTRACT

A wild bee nesting domicile comprising a strip assembly of a flexible backing sheet to which is secured a matching pleated strip, the strip assembly being rolled or wrapped about itself so that the tips of the pleats are in contact with the backing sheet to form closely spaced bee nesting bores. A backing member is secured to the roll to close one end of the nesting bores as preferred by the wild bees. The domicile may be rolled into circular or oblong form, or may comprise a stack of such strips.

9 Claims, 10 Drawing Figures 4,491,994

WILD BEE NESTING DOMICILE

BACKGROUND OF THE INVENTION

1. Field:

The field of the invention is nesting domiciles for wild bees for the propagation of such bees for pollination of plants such as alfalfa.

2. Prior Art:

At least one species of wild bee, (megachile rotundata fabricius), commonly known as the alfalfa leaf-cutter bee, is of considerable economic importance in the northwest United States and Canada, because it, unlike the familiar honey bee, efficiently pollinates alfalfa. The leaf-cutter bees are "solitary", in that they build individual nests and do not cooperate in the gathering and storing of food. However, they are gregarious, and do not resist nesting closely together. Pre-existing holes, such as cells of abandoned wasp nests and bug burrows in wood, are commonly used for nesting bores, in which they construct several nesting cells end to end. Artificial domiciles with many nesting burrows can therefore provide for the propagation of sufficient leaf-cutter bees for thorough pollination of adjacent alfalfa, especially since these bees gather nectar only near their nesting site, whereas honey bees forage miles from their hives. The more primitive previous bee-nesting devices have simulated insect burrows by providing monolithic wooden blocks with drilled, closely spaced bores. More advanced devices utilized wooden laminations held together mechanically, the nesting bores being surface grooves in the individual laminations. They may be disassembled for inspection of the rows of bee-hatching cells for disease, fungus or insect attack. Barber, U.S. Pat. No. 3,936,894, has laminations with surface grooves, closed by the ungrooved surface of the adjacent lamination. A central bore accepts a bolt which is used with end plates to hold the laminated assembly together. Dority, U.S. Pat. No. 3,267,497, comprises a series of wooden blocks with aligned bores, again held together by bolts and nuts. Another similar bank of grooved blocks is disclosed in Barnes Jr., U.S. Pat. No. 3,191,199, having matching semicircular grooves in the adjacent bores of the laminations, providing circular nesting bores. Similar laminated structures may be made of plastic, as disclosed in Publication 1495, 1973 entitled "Alfalfa Leaf-cutter Bees for Pollinating the Alfalfa in Western Canada", and the advertising sheet "The Bords and the Bees", both accompanying this application. The grooved wood or plastic constructions are unnecessarily expensive to construct and the wood often swells from moisture, closing the nesting bores to smaller unacceptable sizes. Both are unnecessarily prone to mold growth from moisture accumulation. The wooden versions are unnecessarily heavy, and require tools for assembly and disassembly. Stripping of the individual cells from the essentially rigid laminations, for bulk shipment or for loose cell management, often necessitates the use of complicated and expensive machinery. These current bee domiciles are difficult to clean and disinfect before reuse, and are sufficiently expensive to make their discard a matter of economic concern.

BRIEF SUMMARY OF THE INVENTION

With the foregoing in mind the present invention eliminates or substantially alleviates the disadvantages in the prior art of wild bee nesting devices by providing an alongate flexible strip assembly comprising a thin flexible backing strip preferably of porous paper, along one surface of which is secured a pleated strip of similar material forming adjacent open channels transverse to the backing strip. The elongate strip assembly is preferably wound into a roll, so that the open side of each channel is closed by the other surface of the backing strip to form a multiplicity of closely spaced bores in each of which the wild bees construct several individual nesting cells end to end. The nesting bores are all closed at one end as required by the wild bees, preferably by a flat sheet of similar material. The elongate strip assembly may be wound upon a circular central core cylinder, resulting in a circular bee domicile with many closely spaced nesting bores. Rectangular cores or other shapes can also be used to provide domiciles of varying shapes, should such be desired as for improved packaging density for shipment. The nesting domicile may be secured to a vertical or horizontal support structure with the nesting bores opening outwardly horizontally or downward vertically. Between each two adjacent nesting bores is a small generally triangular bore, formed between the pleated and backing strips which is however too small for nesting purposes and not used by the wild bees. Every nesting cell in every bore may be inspected for disease, mold or the like by removing the bore closing sheet and unwinding the strip assembly exposing the cells in the channels to view. Advantageously, the bore closing sheet is secured by non-hardening adhesive, to facilitate its removal. The nesting cells are easily dislodged undamaged should their harvest be desired. Preferably, the flexible backing and pleated material is thin ordinary packaging or box paper advantageously porous for moisture dissipation. Although plastic sheet material could be utilized, it is not preferred because of its relative impermeability to moisture. According to one aspect of the invention, an elongate flexible spacer strip may be wound with the flexible strip assembly to provide landing area for the wild bees. According to another aspect, discrete lengths of the elongate strip assembly may be secured in stacked relationship to provide the nesting bores.

It is therefore a major object of the invention to provide a high density nesting domicile for wild bees which is easily disassembled for inspection and harvesting, resistant to mold formation, and economical enough for disposal after one use.

BRIEF DESCRIPTION OF THE DRAWINGS

In the drawings, which represent the best modes presently contemplated for carrying out the invention.

DETAILED DESCRIPTION OF ILLUSTRATED EMBODIMENTS

Figure 1:
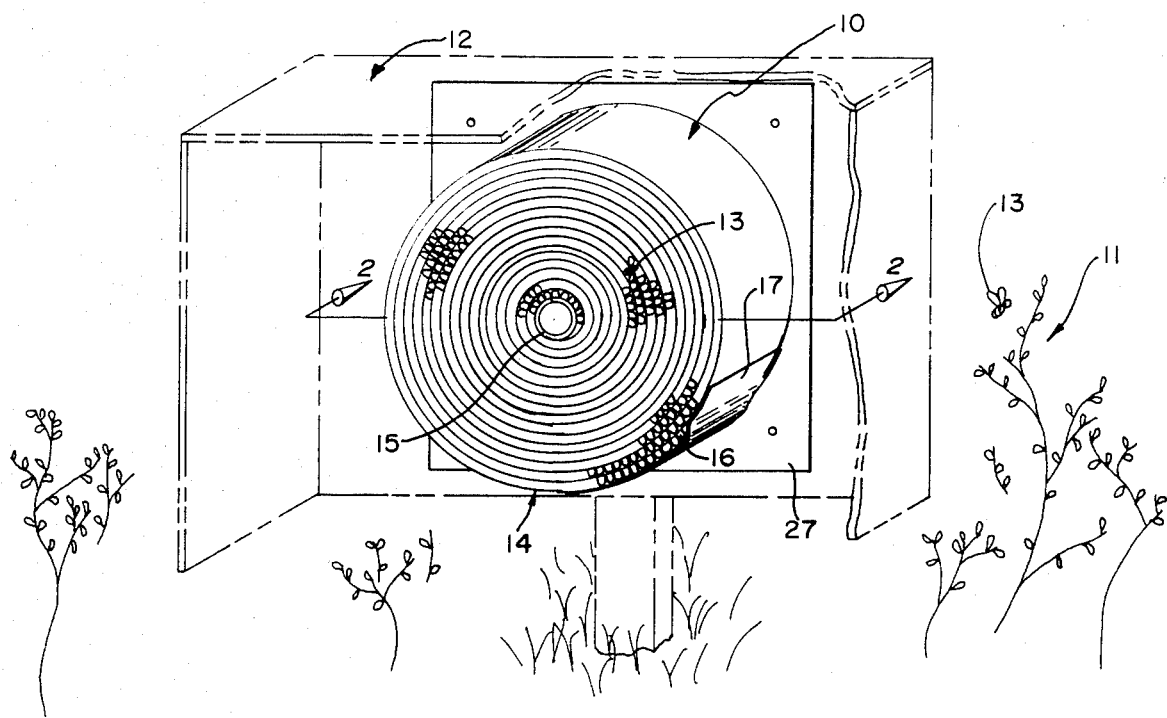
FIG. 1 is a perspective view of a wild bee nesting domicile in accordance with the invention drawn to a reduced scale, and illustrated in use in a field of alfalfa, FIG. 2 an end view of the domicile of FIG. 1, taken along line 2—2 thereof, drawn to substantially full scale, FIG. 3 a cross sectional view of a fragment of the domicile of FIG. 2, taken along line 3—3 thereof, drawn to the same scale.

A single wild bee nesting domicile 10 in accordance with the invention is illustrated in FIG. 1, secured within an open sided shelter 12 for use in a field of alfalfa 11. Wild bees 13 are shown pollinating the alfalfa 11 and utilizing the domicile 10 for nesting. Domicile 10 may be of shapes other than circular, and several may be used mounted together within a single shelter.

Figure 2:
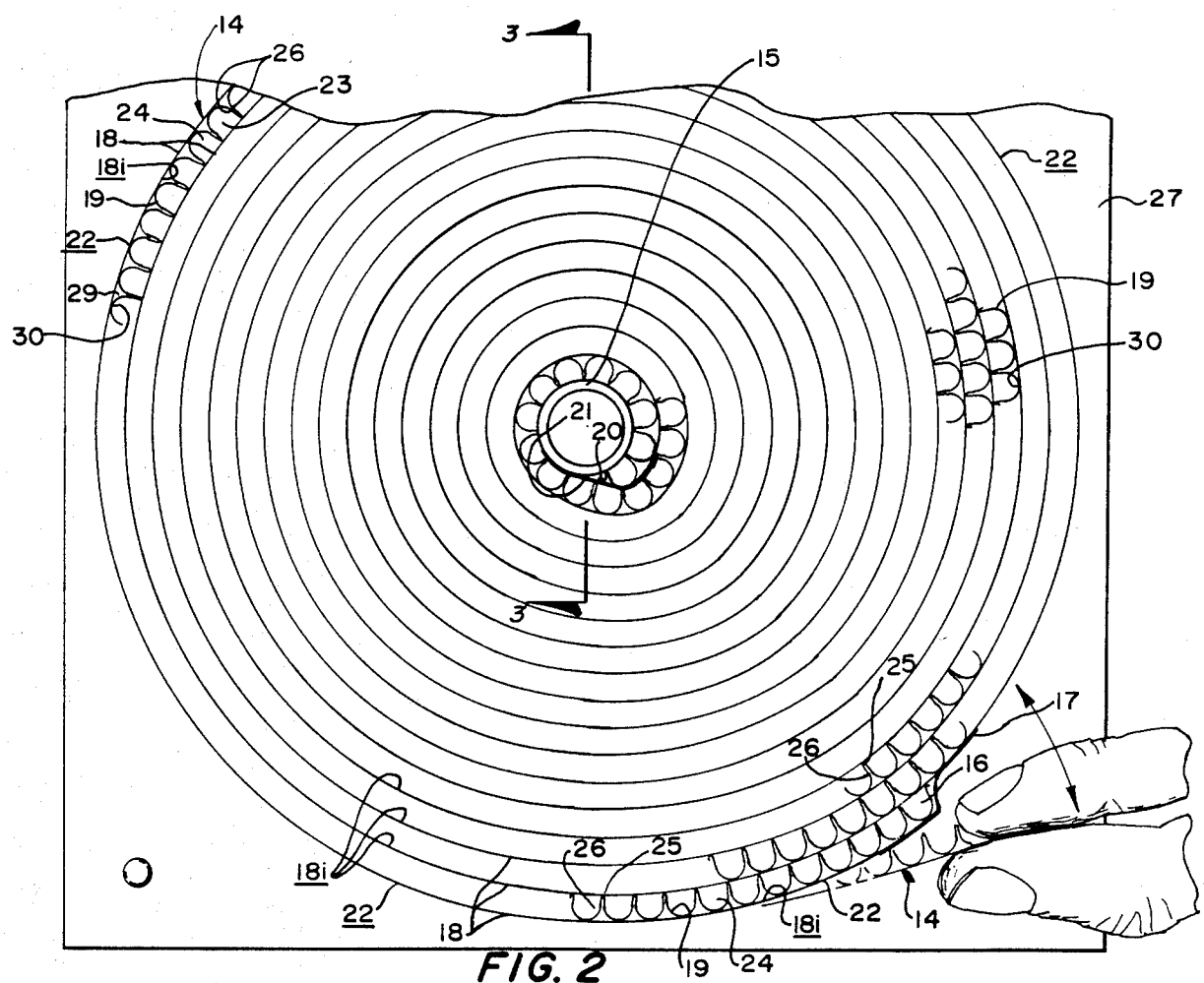
Figure 3:
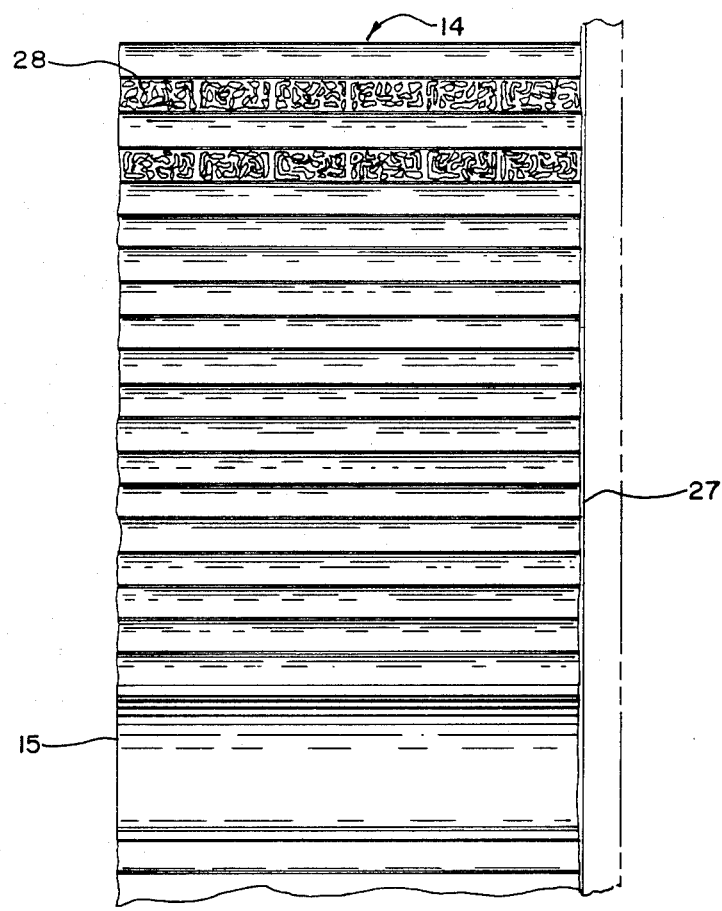

The illustrated domicile 10 comprises an elongate, flexible pleated strip assembly 14 wound into a roll about a circular core 15, with its outside end 16 secured as by adhesive tape 17 to prevent unwinding. Strip assembly 14 has a flexible backing member 18 coated on inside surface 18i with adhesive securing a matching pleated strip 19. (FIG. 5.) The inside end 20 of strip 14 is secured, as by adhesive tape 21, to the circular core 15. (FIG. 2.) The uncoated outside surface 22 of backing strip 18 spans across "U" shaped channels 23 between the pleats 26 of member 19, forming closed nesting bores 24. The end cusps 25 of pleats 26 rest preferably unattached against the uncoated surface 22 of backing strip 18. A back cover 27 adheres to domicile 10 and closes one end of all the bores 24, and may also serve as a mounting member as shown in FIG. 1. The wild bees construct nesting cells 28 serially from cover 27 to the opposite side of the domicile 10. (FIGS. 3 and 4.)

Figure 4:
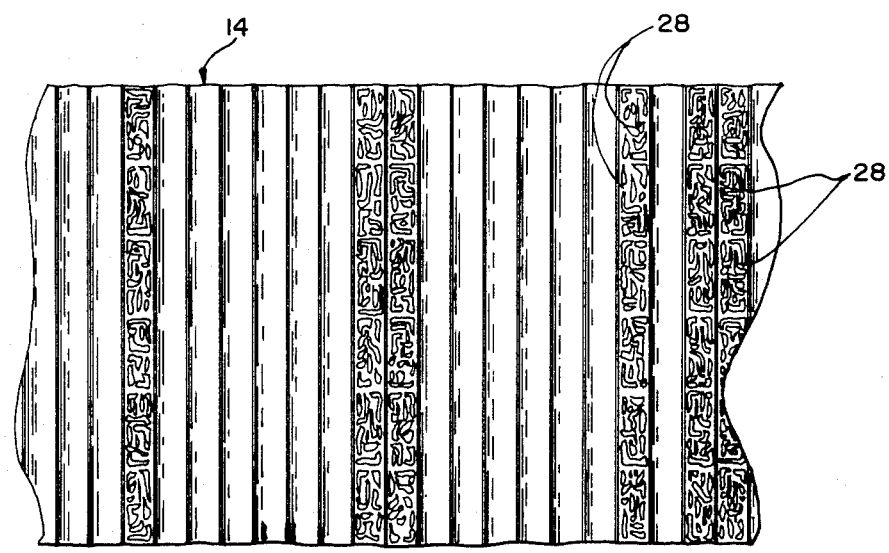
FIG. 4 a view of a fragment of the flexible strip assembly of which the domicile of FIG. 2 is comprised, said fragment being shown in unwound form exposing the individual bee nesting cells, drawn to the scale of FIG. 2.
Figure 5:
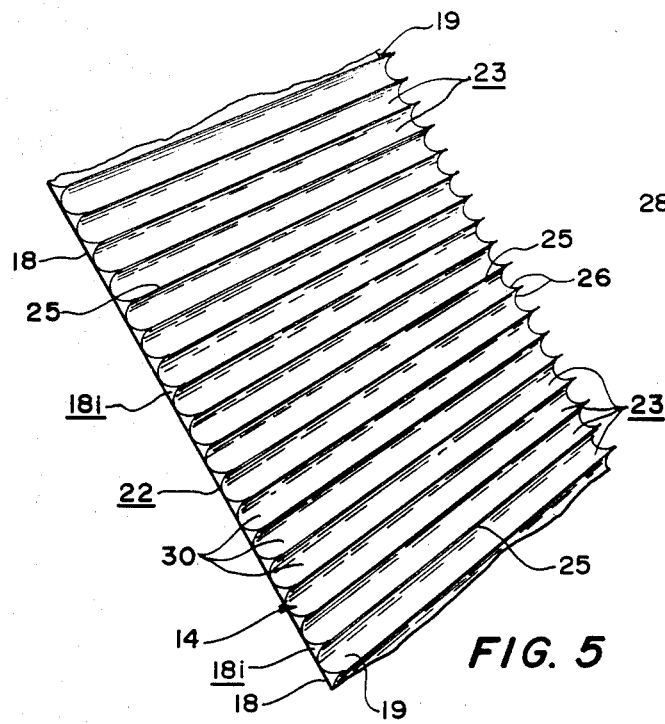
FIG. 5 a perspective view of a fragment of the flexible strip assembly of which the domicile of FIG. 2 is comprised, drawn to approximately the scale of FIG. 2, FIG. 6 an end view of a fragment of a bee domicile having a spacer strip between the flexible pleated strips, drawn to substantially full scale, FIG. 7 an end view of an oblong domicile in accordance with the invention, drawn to a somewhat reduced scale, FIG. 8 a reduced scale perspective view of a domicile in accordance with the invention, comprising a stack of discrete lengths of pleated strips, FIG. 9 a reduced scale perspective view of a domicile in accordance with the invention, comprising a length of single pleated strip with an unpleated channel closing strip added, and FIG. 10 a schematic representation of a machine for constructing the pleated strip assemblies of which the bee domiciles are comprised.

To inspect the nesting cells 28 for disease, mold, fungus or insect parasites, back cover 27 (preferably coated with nonhardening adhesive) is stripped off, and adhesive tape 17 is released, so that strip assembly 14 may be unwound along with nesting cells 28 as indicated in dashed lines in FIG. 2, to expose the nesting cells as seen in FIG. 4. Should the cells 28 be found to be diseased, the entire domicile 10 may be burned to prevent spread of the disease, without great concern because of its low cost. For harvest, the cells 28 are easily dislodged without damage into a container for cold storage and later use, or shipment for cell management elsewhere.

The alfalfa leaf-cutting bee does not require precisely sized or shaped nesting bores 24, and closed "U" shaped bores 24 of 3/16" to ¼" are quite satisfactory for the alfalfa leaf-cutter bee. The closed triangular bores 29 under pleats 26 are purposely too small for the alfalfa leaf-cutter bee. Larger or smaller bores 24 may be required for other wild bee species which may be more adapted for pollination of crops other than alfalfa. Preferably the material of the backing strip 18 and pleated strip 19 is thin paper commonly used for packaging or the like. Such material is very flexible, and is advantageously porous to dissipate moisture to combat harmful mold formation. Other materials such as thin flexible plastic may also be used but are less desirable because they are not normally porous and tend to retain moisture.

Figure 10:
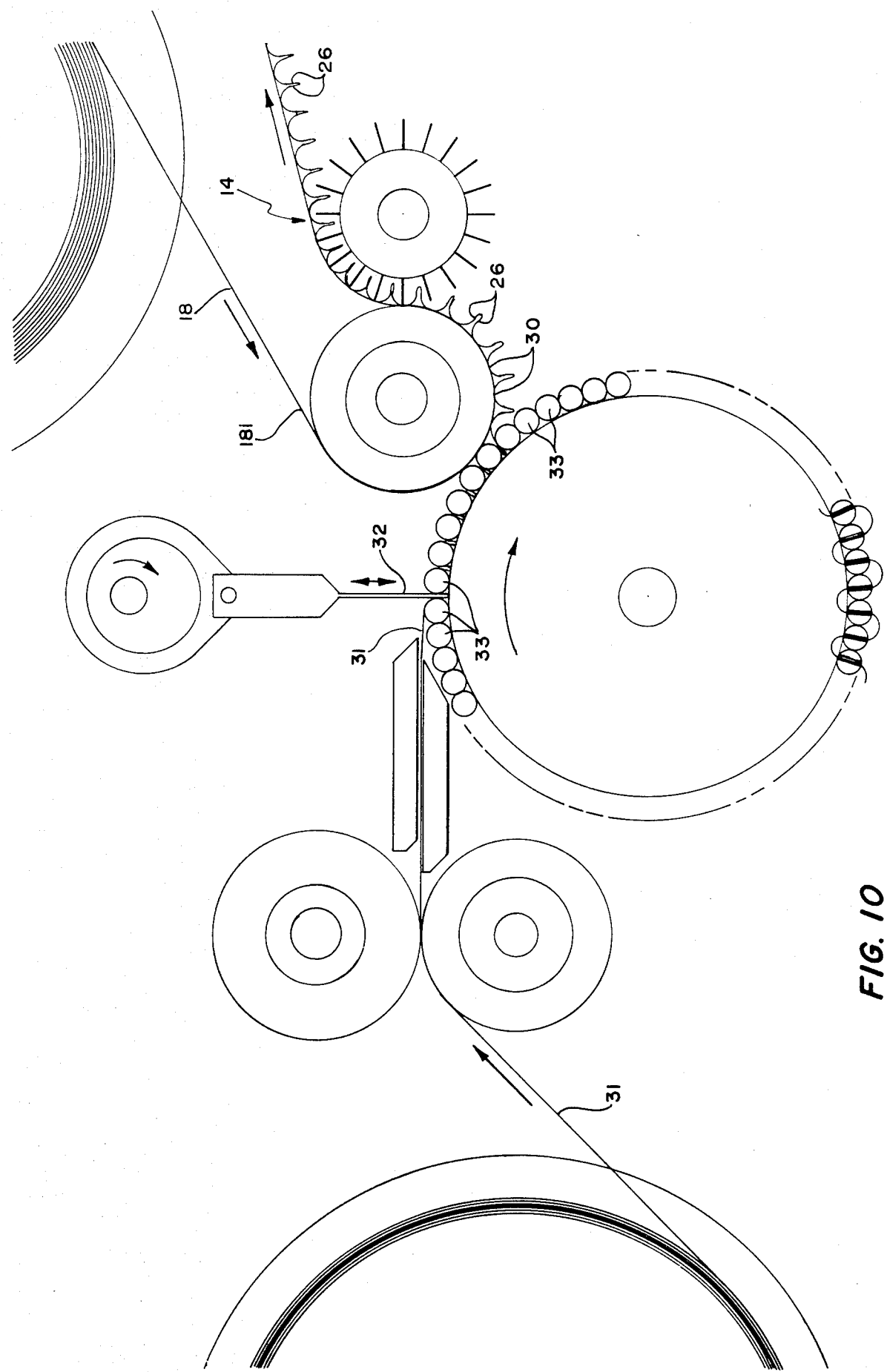

As previously described, one side of backing strip 18 is provided with an adhesive coating, which secures the roots 30 of pleats 26 to backing strip 18, so that strip assembly 14 may be wound as illustrated without too much distortion of channels 23 or the resulting nesting bores 24. Accordingly, both backing strip 18 and pleated strip 19 may be of quite thin paper, for great flexibility and very low material cost. Strip assembly 14, with the very thin paper, the small "U" shaped channels 23, and the small openings 29, is not to the inventor's knowledge commercially available. It has been constructed as indicated schematically in FIG. 10. The pleats 26 are formed successively from incrementally advanced pleating paper 31 by a reciprocating pleating blade 32 acting between rollers 33. The adhesive coated backing strip 18 is directed into adhering contact with the roots 30 of the pleats 26, drawing pleated strip 19 from the rollers 33 and producing strip assembly 14, which may then be wound loosely upon a storage drum, or upon a core 15 to substantially complete a circular bee domicile 10. With much greater cost and weight and decreased flexibility, pleated strip 19 could conceivably be constructed of heavier, less flexible material, and then wound with backing strip 18 without being secured thereto.

Figure 8:
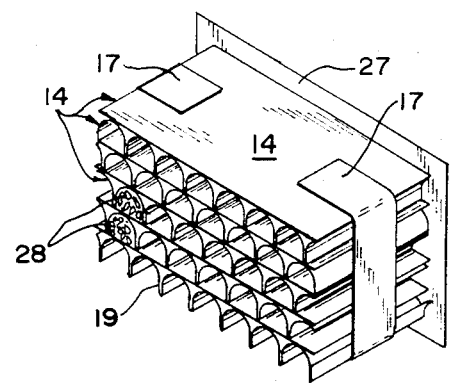
Figure 9:
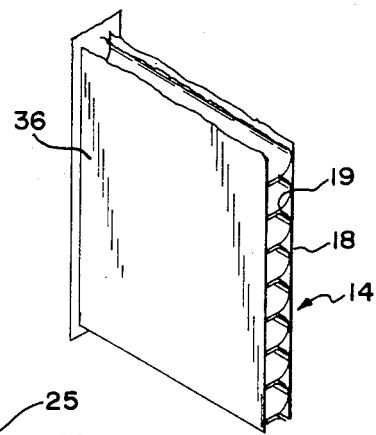
Figure 6:
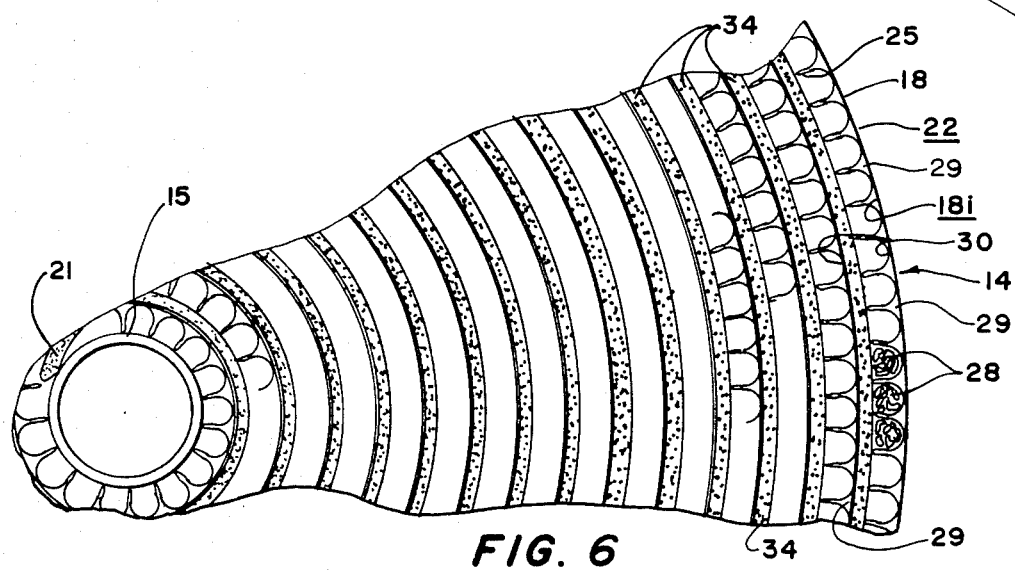
Figure 7:
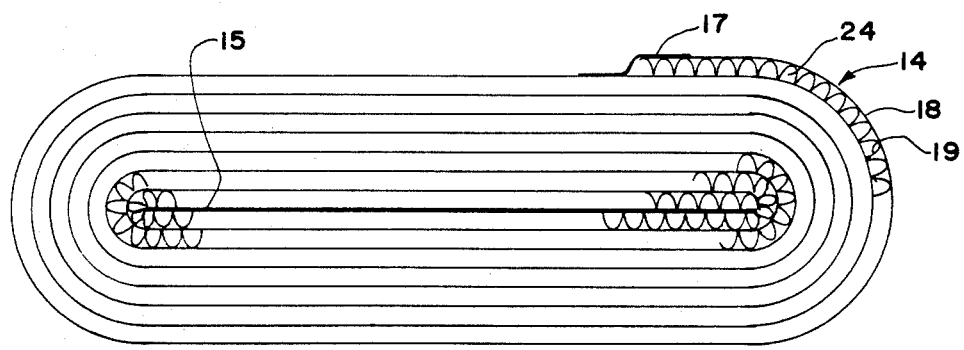

Domiciles 10 of shapes other than circular may be created by selecting a core 15 of the desired shape. For example, an oblong configuration (FIG. 7) is achieved by using a rectangular core member 15, and would provide more densely packaged shipping containers, and more densely utilized shelters. The cores 15 are of convenient materials including wood, pressed wood, plywood, or plastic. Another variation in the structure of bee domicile 10 is shown in FIG. 6. A flexible spacing strip 34, of sponge rubber for example, is utilized between the windings of strip assembly 14, and provides landing area for the bees. This may be important when large numbers of bees simultaneously engage in nesting activities. As with the previously described structure of domicile 10, the nesting strips 14 and the spacing strips 34 may be unwound for inspection and harvesting of the cells. Another, but less desirable, embodiment of domicile 10 is illustrated in FIG. 8., comprising a stack of discrete generally planar strip assemblies 14 secured together as by adhesive tape 17, and having the backing member 27. In this embodiment, the backing strip 18 is desirably of substantial thickness to provide rigidity to domicile 10, which is correspondingly heavier and more expensive to fabricate in comparison with the other, more preferred illustrated embodiments. Conceivably, the pleated strip 19 could be made of substantially rigid material and left unattached to backing strip 18. Still other embodiments may be employed within the spirit of the invention. For example, a single elongate strip could be used in straight form in conjunction with a single matching straight facing strip similar to the backing strip 18. (FIG. 9)

To insure that the return of newly emerging bees to the newly constructed domicile, loose cells containing bee prepupae may be placed as a thin layer in a container, and the paper nesting material placed snugly upon the cells. The container and the domicile may be fastened within a shelter as described previously for the domicile alone. The paper may be impregnated with attractants for nesting females, or with specific insecticides or repellants to combat insect, parasites, and predators.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A wild bee nesting domicile having a multiplicity of wild bee nesting bores, said domicile comprising:
   a continuous elongate strip assembly of thin flexible sheet paper comprising a pleated strip, a matching elongate backing strip and means securing the pleated strip with the roots of the pleats against one of the surfaces of the backing strip, said continuous strip assembly being secured in rolled form so tht the tips of the pleats are against adjacent portions of the other surface of the backing strip so that the pleated strip forms with the backing strip a multiplicity of nesting bores, each bore extending longitudinally from one end of the rolled strip assembly to the other end thereof, all of said nesting bores being on the same side of said pleated strip; and
   a closure member secured against one end of the rolled strip assembly so as to close one end of each of the nesting bores.

2. The domicile of claim 1, wherein:
the means securing the pleated strip to the backing strip comprises adhesive means.

3. The domicile of claim 2, wherein:
the strip assembly is rolled so that the domicile is of generally circularly cylindrical form.

4. The domicile of claim 2, wherein:
the strip assembly is rolled so that the domicile is of generally oblong form.

5. The domicile of claim 2, wherein:
the bore closure member is of thin paper and is adhesively secured to the rolled strip assembly.

6. A wild bee nesting domicile having a multiplicity of wild bee nesting bores, said domicile comprising:
   at least one elongate strip assembly comprising a pleated paper strip, an unpleated paper backing strip matching the pleating strip, and means securing the pleated strip to the matching backing strip;
   an unpleated paper facing strip matching the strip assembly and secured against the pleated strip of the strip assembly to form therewith the multiplicity of nesting bores from one side of the strip assembly to the other, all of said nesting bores being on the same side of said pleated strip; and
   means closing one end of each of the nesting bores.

7. The domicile of claim 6, wherein:
the means closing the bores is a narrow strip of paper sheet adhesively secured along one edge of the elongate strip assembly.

8. A wild bee nesting domicile having a multiplicity of wild bee nesting bores, said domicile comprising:
   a multiplicity of pleated paper sheets and a matching multiplicity of matching unpleated paper sheets, said pleated and unpleated sheets being secured together in alternating stacked relationship, so as to together form the multiplicity of nesting bores from a side of the stack to the opposite side thereof, all of said nesting bores of each pleated sheet being on the same side of said sheet; and
   means closing one end of each of the bores.

9. The domicile of claim 8, wherein:
each of the pleated sheets is adhesively secured to one of the unpleated sheets at the roots of the pleats to form a multiplicity of sheet assemblies, said sheet assemblies being secured together to form a stack having the multiplicity of nesting bores, each of the bores extending from a side of the stack to the other side thereof.

* * * * *